United States Patent [19]
Lyssikatos et al.

[11] Patent Number: 5,948,781
[45] Date of Patent: Sep. 7, 1999

[54] ADAMANTYL SUBSTITUTED OXINDOLES AS PHARMACEUTICAL AGENTS

[75] Inventors: Joseph P. Lyssikatos, Gales Ferry; Robert A. Volkmann, Mystic, both of Conn.

[73] Assignee: Pfizer Inc, New York, N.Y.

[21] Appl. No.: 08/863,514

[22] Filed: May 27, 1997

Related U.S. Application Data

[60] Provisional application No. 60/018,490, May 28, 1996.
[51] Int. Cl.$^6$ ............... C07D 401/06; C07D 401/14; A61K 31/44; A61K 31/505
[52] U.S. Cl. ............... 514/256; 544/333; 544/405; 544/238; 544/295; 544/296; 544/182; 544/180; 544/179; 544/357; 544/373; 546/186; 546/187; 546/256; 546/277.7; 514/241; 514/242; 514/253; 514/316; 514/323; 514/333; 514/339
[58] Field of Search ............... 544/333, 405; 546/256, 277.7; 514/253, 256, 333, 339

[56] References Cited

U.S. PATENT DOCUMENTS 4,760,083   7/1988   Myers et al. ............... 514/333

OTHER PUBLICATIONS

Graham, "Inhibitors of Protein Farnesylation: A New Approach to Cancer Chemotherapy," Exp. Opin. Ther. Patents, vol. 5, No. 12, pp. 1269–1285, 1995.

Nagasu et al., "Inhibition of Human Tumor Xenograft Growth by Treatment with the Farnesyl Transferase Inhibitor B956," Cancer Research, vol. 55, pp. 5310–5314, 1995.

Primary Examiner—Mukund J. Shah
Assistant Examiner—Ann M. Kessinger
Attorney, Agent, or Firm—Peter C. Richardson; Paul H. Ginsburg; Raymond M. Speer

[57] ABSTRACT

This invention relates to a method of treating cancer by administering a compound of the formula

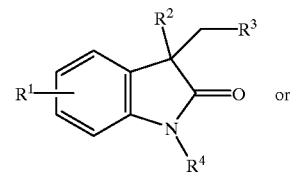

IA or

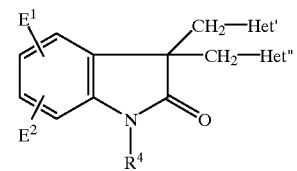

IB wherein $R^1$, $R^2$, $R^3$, $R^4$, $R^5$, $E^1$, $E^2$, p, Het' and Het" are defined as indicated in the specification.

10 Claims, No Drawings

ADAMANTYL SUBSTITUTED OXINDOLES AS PHARMACEUTICAL AGENTS

This application claims benefit of Provisional Application 60/018,490 filed May 28, 1996.

This invention relates to the use of certain substituted heterocyclic compounds for the treatment of cancer. The therapeutically active agents of this invention exhibit activity as inhibitors of the enzyme farnesyl protein transferase and are believed to be useful as anti-cancer and anti-tumor agents.

Other compounds that inhibit farnesyl protein transferase and are believed to be useful as anti-cancer and anti-tumor agents are referred to in International Patent Application PCT/US 92/11292, which designates the United States and was published on Jul. 22, 1993 as WO 93/14085, U.S. Pat. No. 4,876,259, which issued on Oct. 24, 1989, International Patent Application PCT/IB95/00189 filed on Mar. 20, 1995 and published on Nov. 9, 1995, as WO 95/29909, and U.S. patent application Ser. No. 08/737,376 filed on Mar. 20, 1995 and issued on Dec. 29, 1998 as U.S. Pat. No. 5,854,232.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

SUMMARY OF THE INVENTION

This invention relates to compounds of the formula

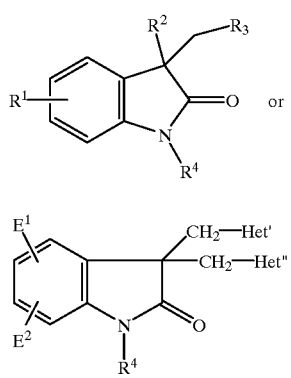

wherein $R^1$ is hydrogen, halo (e.g., chloro, fluoro, bromo or iodo), cyano, hydroxy, nitro, trifluoromethyl, —$NHR^5$, —$NR^5R^5$, $R^5$, —$OR^5$ or —$S(O)_m$—$R^5$;

$R^2$ is —$(CH_2)_n$—Y or —$OCOR^5$;

$R^3$ is 4-, 3-, or 2-pyridyl, pyrimidyl, pyrazinyl, 2-fluoro4-pyridyl or 3-fluoro-4-pyridyl;

$R^4$ is 1-adamantyl or 2-adamantyl;

Y is hydrogen, hydroxy, amino, cyano, —$NHR^5$, —$NR^5R^5$, —$NHCOR^5$, —$NHCO_2R^5$, halo, $OR^5$, —$S(O)_mR^5$, —$CO_2H$, —$CO_2R^5$, —$CONR^5R^5$, —$CONHR^5$, —$CONH_2$, —$COR^5$, —$CH$=$CHCO_2R^5$, —$OCOR^5$, phenyl, phenyl substituted with W, —$C$≡$CCO_2R^5$, —$CH$=$CHR^5$ or —$C$≡$CR^5$;

each $R^5$ is, independently, ($C_1$–$C_4$) straight or branched alkyl, phenyl or benzyl, wherein said phenyl and the phenyl moiety of said benzyl may optionally be substituted with halo, hydroxy, nitro, cyano, amino, ($C_1$–$C_4$) straight or branched alkyl, ($C_1$–$C_4$) straight or branched alkoxy, phenyl, benzyl, ($C_1$–$C_4$)alkylamino, di[($C_1$–$C_4$)alkyl]amino, or —$S(O)_m13$ ($C_1$–$C_4$) straight or branched alkyl;

each W is, independently, halo, $R^5$, hydroxy, —$OR^5$, nitro, amino, —$NHR^5$, —$NR^5R^5$, cyano, or —$S(O)_m$—$R^5$;

m is 0, 1 or 2;

n is 1 to 7;

$E^1$ and $E^2$ are selected, independently, from hydrogen, halo, ($C_1$–$C_3$)alkyl, hydroxy, ($C_1$–$C_3$)alkoxy, nitro, trifluoromethyl, cyano, amino, ($C_1$–$C_3$)alkylamino and di[($C_1$–$C_3$)alkyl]amino;

Het' and Het" are selected, independently, from 6 membered heterocyclic rings containing from one to four nitrogen atoms as part of the ring, optionally substituted with one substituent selected from ($C_1$–$C_3$)alkyl, halo, hydroxy, ($C_1$–$C_3$)alkoxy, amino, ($C_1$–$C_3$) alkylamino and di[($C_1$–$C_3$)alkyl]amino;

and their pharmaceutically acceptable salts.

More specific embodiments of this invention include the following:

(a) compounds of the formula IA wherein $R^3$ is 4-pyridyl, 4-pyrimidyl or 2-fluoro-4-pyridyl;

(b) compounds of the formula IA wherein $R^2$ is —$(CH_2)_nY$;

(c) compounds of the formula IA wherein $R^2$ is —$(CH_2)_nY$ and n is an integer from 1 to 5;

(d) compounds of the formula IA or IB wherein each of $R^1$, $E^1$, and $E^2$ is hydrogen; and (e) compounds of the formula IA wherein $R^2$ is —$(CH_2)_n$—Y, $R^1$ is 4-pyridyl, 4-pyrimidyl or 2-fluoro-4-pyridyl, $R^5$ is ($C_1$–$C_2$) alkyl and Y is —$CO_2R^5$, cyano, —$CONHR^5$, —$CH$=$CHCO_2R^5$ or —$OCOR^5$.

Other more specific embodiments of this invention relate to compounds of the formula IA wherein the $R^5$ groups are other than a phenyl or benzyl group that is substituted with either a phenyl or benzyl group. Other more specific embodiments of this invention relate to compounds of the formula IA wherein none of the $R^5$ groups is substituted or unsubstituted phenyl or benzyl.

This invention also relates to a method of inhibiting the abnormal growth of cells in a mammal, including a human, comprising administering to said mammal a farnesyl protein transferase inhibiting effective amount of a compound of the formula IA or IB, as defined above, or a pharmaceutically acceptable salt of such a compound.

This invention also relates to a method of inhibiting the abnormal growth of cells in a mammal, including a human, comprising administering to said mammal an abnormal cell growth inhibiting effective amount of a compound of the formula IA or IB, as defined above, or a pharmaceutically acceptable salt of such a compound.

This invention also relates to a pharmaceutical composition for inhibiting the abnormal growth of cells in a mammal, including a human, comprising a farnesyl protein transferase inhibiting effective amount of a compound of the formula IA or IB, as defined above, or a pharmaceutically acceptable salt of such a compound, and a pharmaceutically acceptable carrier.

This invention also relates to a pharmaceutical composition for inhibiting the abnormal growth of cells in a mammal, including a human, comprising and administering to said mammal and abnormal cell growth inhibiting effective amount of a compound of the formula IA or IB, as defined above, or pharmaceutically acceptable salt of such a compound, and pharmaceutically acceptable carrier.

"Abnormal cell growth", as used herein, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Examples of such benign proliferative diseases are psoriasis, benign prostatic hypertrophy and restinosis.

The term "alkyl", as used herein, unless otherwise indicated, includes saturated monovalent hydrocarbon radicals having straight, branched or cyclic moieties or combinations thereof.

The term "halo", as used herein, refers to chloro, fluoro, bromo or iodo.

The compounds of formulae IA and IB that are basic in nature are capable of forming a wide variety of salts with various inorganic and organic acids. The acids that may be used to prepare pharmaceutically acceptable acid addition salts of those compounds of formulae IA and IB that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

The compounds of formulae IA and IB above may contain chiral centers and therefore may exist in different enantiomeric forms. This invention relates to all the optical isomers and other stereoisomers of compounds of the formulae IA and IB, as well as racemic and other mixtures of such isomers.

Patients that can be treated with compounds of the formula IA or IB according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

Patients that can be treated with compounds of the formula IA or IB according to the methods of this invention also include patients suffering from abnormal cell growth, as defined above.

DETAILED DESCRIPTION OF THE INVENTION

The preparation of compounds of the formulae IA and IB are described below. In the reaction schemes and discussion that follow, Y, W, $R^1$, $R^1$, $R^2$, $R_4$, $R^5$, $E^1$, $E^2$, Het' and Het" are defined as above.

Scheme 1

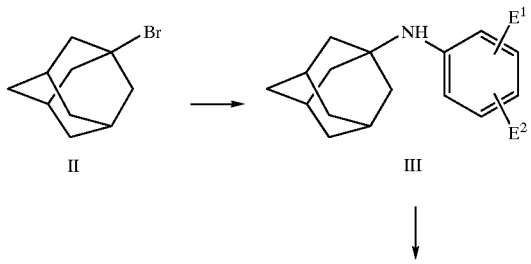

II  III

-continued
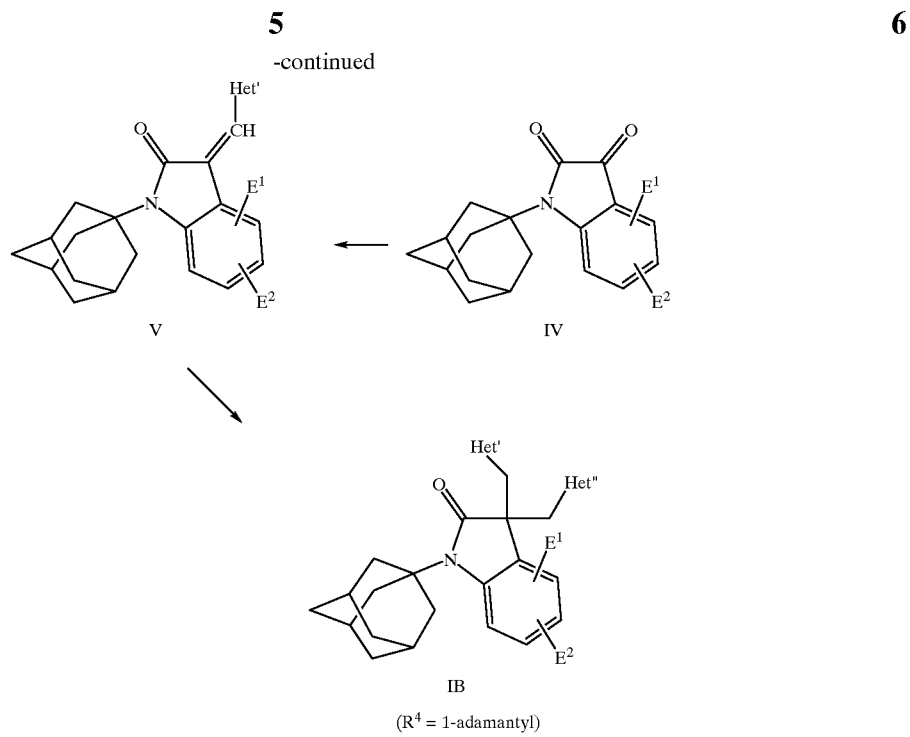
(R⁴ = 1-adamantyl)
Scheme 2
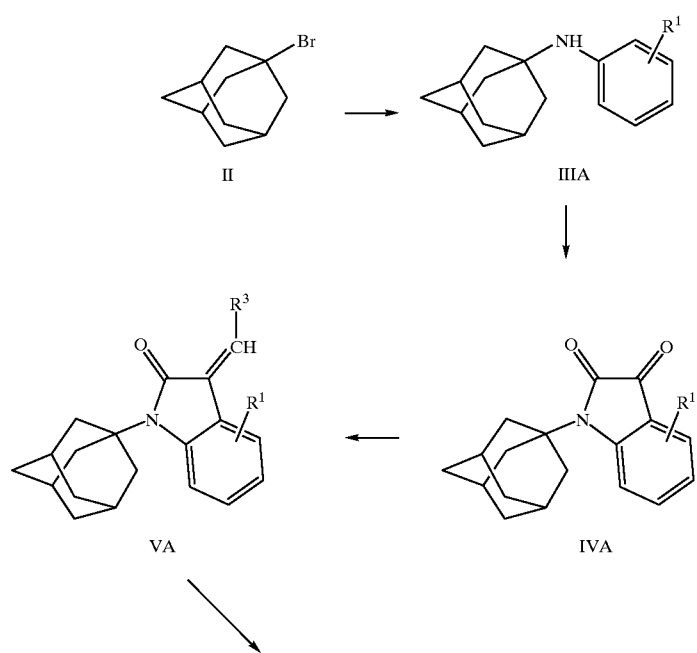

-continued

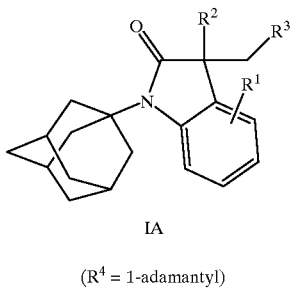

IA ($R^4$ = 1-adamantyl)

Scheme 1 illustrates the synthesis of compounds of the formula IB wherein $R^4$=1-adamantyl. Compounds of the formula IB wherein $R^4$ is 2-adamantyl can be prepared by the same process starting with the 2-adamantyl analog of compound II.

Referring to Scheme 1, 1-bromoadamantyl (formula II) is reacted with aniline or an aniline derivative of the formula

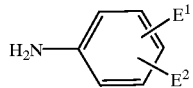

VI to form the adamantyl substituted aniline derivative of formula III. This reaction is generally carried out neat at a temperature from about 150° C. to about 250° C., preferably at about 200° C. The compound of formula III is then reacted with oxalyl chloride to form the substituted benzopyrrolidine of formula IV. Typically, this reaction is carried out in an aprotic solvent such as benzene or toluene, preferably toluene, at a temperature from about 0° C. to about 80° C., preferably at about 65° C.

Reaction of the resulting compound of formula IV with a compound of the formula $CH_3$-Het' in an acetic acid/acetic anhidride mixture yields the corresponding compound of formula V. The temperature for this reaction can range from about 100° C. to about 160° C., and is preferably about 140° C.

The compound of formula V so formed can be converted into the desired compound of formula IB by the following two step process. First, the compound of formula V is reacted with a reducing agent such as sodium triacetoxy borohydride or sodium borohydride in methanol or ethanol, preferably sodium borohydride in methanol, at a temperature of about 0° C. to about 30° C., preferably at about 5° C., to reduce the carbon-carbon double bond of the Het'—CH=sidechain. Then, the Het"—$CH_2$ substituent is added in situ, or after isolating the product of the foregoing reaction, by reacting the foregoing reaction mixture, or the isolated product, as the case may be, with Het"—$CH_2X$, wherein X is an appropriate leaving group such as chloro or bromo, in the presence of a strong base such as potassium hydroxide in methanol or sodium hydride in either tetrahydrofuran (THF), ether or dimethoxy ethane (DME), preferably potassium hydroxide in methanol or sodium hydride in THF. This reaction is typically carried out at a temperature from about 0° C. to about 60° C. Preferably the reaction temperature is from about 20° C. to about 30° C. If the reaction with Het—$CH_2X$ is carried out in situ, it is helpful to add potassium hybroxide to the mixture as a solubilizer.

Scheme 2 illustrates the synthesis of compounds of the formula IA wherein $R^4$ is 1-adamantyl. The corresponding compounds wherein $R^4$ is 2-adamantyl can be prepared in the same manner starting with the 2-adamantyl analog of compound II.

Referring to Scheme 2, the compounds having formulae IIIA, IVA and VA can be prepared as described above for the formation of compounds having the formulae III, IV and V, respectively, with the exception that the reagent of formula VI is replaced with a compound of the formula

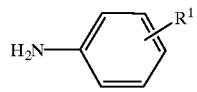

VIA and the reagent of formula methyl-Het' is replaced with a compound of the formula $CH_3R^3$.

The desired product of formula IA can then be formed as follows. The compound of formula VA is first reacted with potassium bis(trimethylsilyl)amide in THF at a temperature from about −70° C. to about 60° C., preferably at about 0° C. Then, after stirring for about 30 minutes, a compound of formula $R^2X$, wherein X is an appropriate leaving group (e.g., chloride or bromide), is added and the reaction mixture is allowed to warm to about ambient temperature.

World Patent Application WO 93/14085, referred to above and incorporated herein by reference in its entirety, describes a method of preparing compounds that differ from those of the formula IA in that there is no adamantyl substituent on the ring nitrogen.

U.S. patent application Ser. No. 4,876,259, also referred to above and incorporated herein by reference in its entirety, describes methods of synthesizing compounds that differ from those of the formula IB in that there is no adamantyl substituent on the ring nitrogen.

The starting materials used in the processes of Schemes 1 and 2 are either known in the literature or commercially available.

The compounds of the formulae IA and IB that are basic in nature are capable of forming a wide variety of different salts with various inorganic and organic acids. Although such salts must be pharmaceutically acceptable for administration to animals, it is often desirable in practice to initially isolate the compound of formula I, IA and IB from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The compounds of the formulae IA and IB exhibit activity as Ras farnesylation inhibitors and are useful in the treatment of cancer and the inhibition of abnormal cell growth in mammals, including humans.

Patients that can be treated with compounds of the formula IA or IB according to the methods of this invention include, for example, patients that have been diagnosed as having lung cancer, bone cancer, pancreatic cancer, skin cancer, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e., cancer of the thyroid, parathyroid or adrenal glands), sarcomas of soft tissues, cancer of the urethra, cancer of the penis, prostrate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

The compounds of formulae IA and IB and their pharmaceutically acceptable salts (hereinafter referred to, collectively, as "the therapeutic compounds") can be administered orally, transdermally (e.g., through the use of a patch), parenterally or topically. Oral administration is preferred. In general, compounds of the formula I and their pharmaceutically acceptable salts are most desirably administered in dosages ranging from about 1.0 mg up to about 500 mg per day, preferably from about 1 to about 100 mg per day in single or divided (i.e., multiple) doses. Compounds of the formulae IA and IB and their pharmaceutically acceptable salts will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers indude solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The activity of the therapeutic compounds as ras farnesylation inhibitors may be determined by their ability, relative to a control, to inhibit ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/$MgCl_2$/ EDTA buffer (using a Dounce homogenizer; 10–15 strokes), centrifuging the homogenates at 1000 grams for 10 minutes at 4 G, re-centrifuging the supernatant at 17,000 grams for 15 minutes at 4 G, and then collecting the resulting supernatant. This supernatant is diluted to contain a final concentration of 50 mM Tris HCl (pH 7.5), 5 mN DTT, 0.2 M KCl, 20 $\mu$M $ZnCl_2$, 1 mM PMSF and re-centrifuged at 178,000 grams for 90 minutes at 4 G. The supernatant, termed "crude FTase" was assayed for protein concentration, aliquoted, and stored at −70° C.

The assay used to measure in vitro inhibition of human Ftase is a modification of the method described by Amersham LifeScience for using their Farnasyl transferase (3H) Scintillation Proximity Assay (SPA) kit (TRKQ 7010). FTase enzyme activity is determined in a volume of 100 $\mu$l containing 50 mM N-(2-hydroxy ethyl)piperazine-N'-(2-ethane sulfonic acid) (HEPES), pH 7.5, 30 mM $MgCl_2$, 20 uM KCl, 5 mM $Na_2HPO_4$, 5 mM dithiothreitol (DTT), 0.01% Triton X-100, 5% dimethyl sulfoxide (DMSO), 20 $\mu$g of crude FTase, 0.12 $\mu$M [3H]-farnesyl pyrophosphate ([3H]-FPP; 36000 dpm/pmole, Amersham LifeScience), and 0.2 $\mu$M of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 μl of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound vs. its incorporation in control wells (absence of inhibitor). $IC_{50}$ values, that is, the concentration required to produce half maximal farnesylation of Bt-KTKCVIS, is determined from the dose-responses obtained.

EXAMPLE 1

1-Adamantyl-1-yl-3,3-bis-pyridin-4-ylmethyl-1,3-dihydro-indol-2-one

A. N-1-Adamantylaniline

Under a nitrogen ($N_2$) atmosphere was combined 10.0 g (46.5 mmol) of 1-bromoadamantane and 20 ml of aniline. The reaction was stirred for 20 hours at 200° C., and then cooled and fractionated on silica gel using 6:1 hexane:ethyl acetate (EtOAc) to afford, after concentration in vacuo and refractionation using toluene, 5.65 g (54%) of N-1-adamantylaniline.

$^1$H NMR (CDCl$_3$) 1.60–1.70 (m-6H), 1.80–1.90 (m-6H), 2.05–2.15 (m-3H), 3.00–3.40 (bs-1H), 6.70–6.80 (m-3H), 7.10–7.20 (m-2H).

$^{13}$C NMR (CDCl$_3$) 29.64, 36.38, 43.37, 52.16, 119.02, 199.08, 128.62, 145.86.

B. 1-Adamantylisatin

Under a $N_2$ atmosphere was added 1.97 g (15.6 mmol) of oxalyl chloride to 3 ml of dry toluene which was cooled to 0° C. To this solution was added 3.55 g (15.6 mmol) of N-1-adamantylaniline in toluene (8 ml). The reaction was allowed to stir for 30 min. at 0° C. and then heated at 65° C. for 3 hours. Additional solvent (10 ml) was added and the reaction was kept at 65° C. for 72 hours. The solvent was removed and the residue was allowed to stir at 160° C. for 5 hours. The crude reaction mixture was allowed to cool and was chromatographed on silica gel using 6:1 hexane:EtOAc to afford crude product, which was triturated with isopropyl ether (IPE) to generate 164 mg (4.4%) of 1-adamantylisatin combined with product contaminated with significant amounts of impurities.

$^1$H NMR (CDCl$_3$) 1.70–1.80 (m-6H), 2.20–2.25 (m-3H), 2.50–2.60 (m-6H), 7.00–7.70 (m-5H).

$^{13}$C NMR (CDCl$_3$) 29.78, 36.14, 40.07, 61.26, 115.62, 118.96, 122.87, 125.51, 137.42, 152.15.

C. 1-Adamantyl-1-yl-3-pyridin-4-ylmethyl-1,3-dihydro-indol-2-one

Under a $N_2$ atmosphere was added 164 mg (0.567 mmol) of 1-adamantylisatin to 2 ml of glacial acetic acid. The suspension was warmed in an oil bath. 4-Picoline (0.091 ml, 0.94 mmol) followed by acetic anhydride (0.094 ml, 1.00 mmol) was added and the solution was allowed to stir at 140° C. for 18 hours. The reaction mixture was cooled and quenched with water. ETOAc was added and the aqueous layer was made basic with sodium bicarbonate (NaHCO$_3$). The organic layer was washed with water followed by brine and then dried over magnesium sulfate, filtered and concentrated in vacuo to afford crude product, which was purified on silica gel using 1:1 ETOAc:hexane to afford 54 mg of starting 1-adamantylisatin and 108 mg (52%) of the desired 1-adamantyl-1-yl-3-pyridin-4-ylmethyl-1,3-dihydro-indol-2-one as a mixture of geometric isomers.

$^1$H NMR (CDCl$_3$) 1.65–1.85 (m-6H), 2.20–2.35 (m-3H), 2.50–2.62 (m-6H), 6.70–7.90 (m-9H), 8.70–8.82 (m-1H).

$^{13}$C NMR (CDCl$_3$) 29.70, 36.09, 39.99, 60.32, 113.75, 113.97, 119.58, 120.94, 121.46, 122.81, 122.87, 124.76, 129.46, 129.63, 131.06, 143.60, 148.79, 150.00.

D. 1-Adamantyl-1-yl-3,3-bis-pyridin-4-ylmethyl-1,3-dihydro-indol-2-one

To a methanol (8 ml) solution at 0–5° C. under a $N_2$ atmosphere containing 1-adamantyl-1-yl-3-pyridin-4-ylmethyl-1,3-dihydro-indol-2-one (100 mg, 0.28 mmol) was added 17 mg (0.45 mg) of sodium borohydride (NaBH$_4$). The reaction mixture was allowed to stir for 45 minutes, at which time 1 ml of water (H$_2$O) followed by 73 mg (1.12 mmol) of potassium hydroxide (KOH) in H$_2$O was added. After 2–3 minutes, 4-picolyl chloride-hydrochloride (49.5 mg, 3 mmol) was added and the reaction was allowed to stir for an additional 15 minutes. Tetrahydrofuran (THF) (2 ml) was added to help solubilize the reactants. After 1 hour, the reaction mixture was concentrated to approximately 5 ml, additional THF was added and the reaction was allowed to stir for 16 hours. The reaction mixture was then concentrated in vacuo and taken up in EtOAc (50 mls). The organic extract was washed with water (3×) and then brine, and then dried over magnesium sulfate and concentrated in vacuo and purified on silica gel using EtOAc to afford 47 mg (38%) of the desired 1-adamantyl-1-yl-3,3-bis-pyridin-4-ylmethyl-1,3-dihydro-indol-2one.

$^1$H NMR (CDCl$_3$) 1.58–1.62 (m-6H), 1.95–2.10 (m-9H), 3.14 (q-4H: JAB=12.5 Hz), 6.70–8.40 (m-8H), 8.20–8.32 (m4H).

$^{13}$C NMR (CDCl$_3$) 29.70, 36.09, 39.99, 60.32, 113.75, 113.97, 119.58, 120.94.

We claim:

1. A compound of Formula (IA) or (IB):

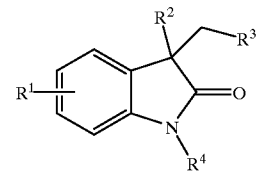

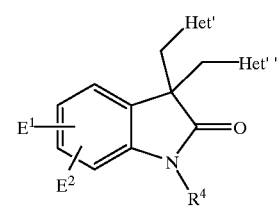

wherein $R^1$ is hydrogen;

$R^2$ is —(CH$_2$)$_n$—Y;

$R^3$ is 4-pyridyl, 4-pyrimidyl, or 2-fluoro-4-pyridyl;

$R^4$ is 1-adamantyl or 2-adamantyl;

Y is cyano, —$CO_2R^5$, —$CONHR^5$, —$CH\!=\!CHCO_2R^5$, or —$OCOR^5$;

each $R^5$ is, independently, ($C_1$–$C_2$) straight or branched alkyl m is 0, 1 or 2;

n is 1 to 5;

$E^1$ and $E^2$ are both hydrogen;

Het' and Het" are both pyridinyl rings optionally substituted with one substituent selected from ($C_1$–$C_3$) alkyl, halo, hydroxy, ($C_1$–$C_3$) alkoxy, amino, ($C_1$–$C_3$) alkylamino and di[($C_1$–$C_3$) alkyl]amino;

or their pharmaceutically acceptable salts.

2. A method of inhibiting abnormal cell growth in a mammal in need of such inhibitory treatment, comprising administering to said mammal a protein farnesyl transferase inhibiting effective amount of a compound of claim 1 as defined therein.

3. A method according to claim 2 of treating breast cancer.

4. A method according to claim 2 of treating bone cancer.

5. A method according to claim 2 of treating lung cancer.

6. A method according to claim 2 of treating pancreatic cancer.

7. A method according to claim 2 of treating skin cancer.

8. A method according to claim 2 of treating prostate cancer.

9. A method according to claim 2 of treating colon cancer.

10. A pharmaceutical composition for inhibiting abnormal cell growth in a mammal, comprising an amount of a protein farnesyl transferase inhibiting compound of claim 1 as defined therein, effective to inhibit said abnormal cell growth, and a pharmaceutically acceptable carrier therefor.

* * * * *